United States Patent
Wegner et al.

(10) Patent No.: US 9,804,090 B2
(45) Date of Patent: Oct. 31, 2017

(54) ENERGY STORE SYSTEM AND STATE DETECTION SYSTEM INCLUDING THE ENERGY STORE SYSTEM

(75) Inventors: Marcus Wegner, Leonberg (DE); Jens Grimminger, Leonberg (DE); Martin Tenzer, Unterensingen (DE); Jean Fanous, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 876 days.

(21) Appl. No.: 14/346,540

(22) PCT Filed: Jul. 17, 2012

(86) PCT No.: PCT/EP2012/063962
§ 371 (c)(1),
(2), (4) Date: Jul. 1, 2014

(87) PCT Pub. No.: WO2013/041262
PCT Pub. Date: Mar. 28, 2013

(65) Prior Publication Data
US 2014/0327911 A1    Nov. 6, 2014

(30) Foreign Application Priority Data
Sep. 22, 2011  (DE) .......................... 10 2011 083 167

(51) Int. Cl.
*H01M 10/44* (2006.01)
*H01M 10/48* (2006.01)
(Continued)

(52) U.S. Cl.
CPC ............. *G01N 21/59* (2013.01); *G01N 21/31* (2013.01); *G01N 21/3577* (2013.01);
(Continued)

(58) Field of Classification Search
CPC .... G01N 21/59; G01N 21/31; G01N 21/3577; H01M 10/44; H01M 10/48
(Continued)

(56) References Cited

U.S. PATENT DOCUMENTS 6,093,292 A  *  7/2000  Akiyama .............. C02F 1/4618
                                                      204/263
2001/0019794 A1 *  9/2001  Horie .................. H01M 10/488
                                                      429/90
(Continued)

FOREIGN PATENT DOCUMENTS

| CN | 1209219 A | 2/1999 |
|---|---|---|
| JP | 2011070932 A | 4/2011 |
| WO | 90/03666 | 4/1990 |

*Primary Examiner* — James Lee
(74) *Attorney, Agent, or Firm* — Norton Rose Fulbright US LLP; Gerard Messina

(57) ABSTRACT

An energy store system, including at least one cell element situated in a cell region having an anode, a cathode and an electrolyte system that is situated between the anode and the cathode and that is particularly at least partially liquid, the anode, the cathode and/or the electrolyte system being configured so that, as a function of a charging or discharging process of the cell element, functioning material is situated in the electrolyte system, and the functional material situated in the electrolyte system being ascertainable qualitatively and/or quantitatively. Because of such an energy store system, operating states of an energy store or a cell may be ascertained particularly simply and accurately. Also described is a related state detection system.

16 Claims, 4 Drawing Sheets

(51) Int. Cl.
 *G01N 21/59* (2006.01)
 *G01N 21/31* (2006.01)
 *G01N 21/3577* (2014.01)
 *G01N 21/33* (2006.01)

(52) U.S. Cl.
 CPC ........... H01M 10/44 (2013.01); H01M 10/48 (2013.01); *G01N 21/33* (2013.01)

(58) Field of Classification Search
 USPC .......................................................... 429/91
 See application file for complete search history.

(56) References Cited

U.S. PATENT DOCUMENTS

2008/0103709 A1    5/2008  Yun et al.
2008/0193828 A1    8/2008  Sahu

\* cited by examiner

ENERGY STORE SYSTEM AND STATE DETECTION SYSTEM INCLUDING THE ENERGY STORE SYSTEM

FIELD OF THE INVENTION

The present invention relates to an energy store system having improved ascertainability of an operating state and having an improved state detection. The present invention also relates to a state detection system including such an energy store system.

BACKGROUND INFORMATION

The state detection and/or a battery management system of an energy store for hybrid or electric vehicles, for example, is able to supply a number of important items of information to the central engine control, in order to ensure at any time the optimum utilization of the energy store and, at the same time, always the reliable functioning and as long a service life as possible. Such information includes, for instance, the stored and the storable energy, the maximum charging and discharging power, the aging condition (state of health, SOH) or the state of function (SOF). These items of information may be ascertained constantly or at specified intervals. Furthermore, a state detection system is able to take over the equilibration of individual ones of the cells connected up in series or in parallel. For this purpose, as precise as possible an ascertainment of the state of charge (SOC) of a plurality of cells is useful.

In order, for instance, to ascertain the state of charge of a lithium ion cell, for example, the use of various algorithms is believed to be understood. In the simplest case, a charge balancing may be undertaken at this point by integration of the flowing current of the energy store. In this context, physical properties may be drawn upon for the state of charge estimation. For example, the fact may be used that the open circuit voltage (OCV) of an electrochemical cell is often able to demonstrate a clear dependence on the state of charge. In order to enable a dynamic method independent of possible waiting times, additional methods for the estimation may be found. For instance, the current state of charge may be determined by integration of the current. In this context, after a rest phase of specified length, a comparison may take place with a table of open circuit voltage. In the broadening of such a method, one may furthermore connect a simulation model for the cell upstream of the determination of the state of charge from the open circuit voltage. This model may be used to determine the voltage deviation from the open circuit voltage under a load, by modeling the impedance of the energy store.

SUMMARY OF THE INVENTION

The subject matter of the present invention is an energy store system including at least one cell element situated in a cell area having an anode, a cathode and an electrolyte system that is situated between the anode and the cathode and that is particularly at least partially liquid, the anode, the cathode and/or the electrolyte system being developed in such a way that, as a function of a charging or discharging process of the cell element, functioning material is situated in the electrolyte system, and the functioning material situated in the electrolyte system is able to be ascertained qualitatively and/or quantitatively.

An energy store system, in this context, is a system which, in particular, has an energy store as the central component.

An energy store, in this context, within the meaning of the present invention, may particularly be an electrochemical component which is able to store and give off energy, such as particularly electrical energy, in a desired manner In particular, an energy store may be a battery or an accumulator. The energy store system may include a lithium-based battery, such as a lithium ion battery, for instance, a lithium sulfur battery.

The energy store system or the energy store may include, in this context, a cell element, having an anode, a cathode and an electrolyte system between them. As a result, the term cell element within the meaning of the present invention is understood to mean the functional element which includes the anode, the cathode and the electrolyte system, or rather particularly is made up of these components and possibly a separator. In this context, the cell element is particularly situated in a cell region. The cell region may thus particularly be formed by the spatial region in which an anode, a cathode and an electrolyte system situated between the anode and the cathode are provided. The cell region is thus, in particular, completely filled up by the cell element of the energy store.

In this context, the electrolyte system may be particularly a liquid, or an at least partially liquid electrolyte system. As a non-limited example, which may possibly be used in the case of a lithium sulfur cell or a lithium sulfur battery as the energy store in the energy store system, let us name here 1,3-dioxolane (DOL)/dimethoxyethane (DME) with lithium-bis-(trifluoromethylsulfonylimide) (LiTFSI).

Furthermore, the anode, the cathode and/or the electrolyte system are developed so that, as a function of a charging and/or discharging process of the functioning material of the cell element is situated in the electrolyte system. Consequently, functioning material may, for instance, be formed or decomposed in the electrolyte system as a function of the state of charge. In this context, the forming or decomposing of the functioning material within the meaning of the present invention may particularly mean that functional material is formed or decomposed directly in the electrolyte system. In addition or alternatively, the functional material may get into the electrolyte system or out of the electrolyte system as a function of the state of charge, possibly by diffusion. Particularly during the providing of an at least partially liquid electrolyte system, the anode, the cathode and/or the electrolyte system may be developed in such a way that the functional material, formed as a function of the state of charge of the cell, dissolves in the electrolyte system. As a non-limiting example, we name here a lithium sulfur cell in which polysulfides dissolve, as intermediate stages of a charging or discharging process, in the electrolyte system. In this case, basically any system is suitable in which functional material, such as active material of anode and/or cathode, is formed or is present which dissolves in the electrolyte system, especially as a function of the state of charge.

In this context, functional material, in the meaning of the present invention, may, in particular, be any compound or substance which is present in the inside of the cell during the operation of the energy store or is able to be formed or decomposed. In particular, the term functional material may include substances of the kind which, for example, are formed and/or decomposed during an electrochemical process running during the charging and/or discharging process of the cell. The concept functional material may, within the meaning of the present invention only include a compound of a substance as was named above, or any mixture of various compounds or substances Because, as a function of a charging or a discharging process of the cell element, functional material is situated in the electrolyte system and, in particularly this case forms or decomposes, this is able to be ascertained, in an especially advantageous manner, qualitatively and/or quantitatively. For example, in the case in which the functional material dissolves in the electrolyte system, a qualitative and/or a quantitative analysis of at least one property of the functional material is able to take place. Furthermore, in response to the presence of a dispersion of the functional material in the electrolyte system, the functional material may also be well able to be analyzed. Because of that, one may draw a conclusion in an especially simple manner on an operating state, such as particularly a state of charge of the energy store system or the cell element.

As a result, because of an energy store according to the present invention, it becomes possible to ascertain, particularly the state of charge, not indirectly by models based on estimates, but perhaps directly, based on an analysis of the electrolyte system or rather, of the functional material situated in the electrolyte system, for instance, dispersed or dissolved. Because the functional material is situated in the electrolyte system as a function of the charging or discharging process, and is there formed and/or decomposed, for example, the state of charge may consequently be ascertained directly, especially based on qualitative, and particularly quantitative measurements. In other words, with the aid of the type detected by a measurement or an analysis, and particularly of the quantity of the functional material, the state of charge may be ascertained when the process taking place during a charging and discharging process is known. In this context, the measurements and the analytical results, especially if compared to a stored charging model, will permit very accurate conclusions upon the state of charge.

Furthermore it becomes possible to ascertain the aging state of the cell or rather, the cell element. This may be implemented particularly by a quantitative, but also by a qualitative measurement of the functional material or the electrolyte material since, by a small concentration of functional material, one is able to draw a conclusion on an active mass loss, for example. This, in turn, may be characteristic for the aging of the cell. A comparison with a suitable aging model may, in this case, supply conclusions on the loss of capacitance of the cell based on the aging phenomenon.

Because of the energy store system according to the present invention, a particularly accurate ascertainment is possible in this context, of an operating state such as the state of charge of an energy store. According to the present invention, erroneous results may be clearly reduced. In particular, no potentially faulty and imprecise estimations have to be carried out.

In addition, particularly rapid and dynamic measurements become possible, which may be made particularly at any time and without awaiting a possible rest period.

In this context, according to the present invention, the problem of the nontrivial, precise modeling of the impedance of an energy store such as a lithium ion battery is circumvented. In particular, the required electrochemical parameters do not have to be identified in a difficult manner. The calculating effort and the storage requirement of a known state detection system may thus be reduced.

Thereby, particular, the accuracy of the determination is able to be improved.

Furthermore, a clear detection of each state of charge, for instance, may take place in the case of lithium sulfur cells. In conventional systems, this may often be difficult up to impossible, since the voltage in such energy stores in relation to time or to the state of charge, that is, particularly their voltage characteristic curves, have plateaus which makes difficult or impossible a unique assignment of each voltage value to a specified state of charge.

Such difficulties are able to be circumvented according to the present invention, since for determining, for instance, the state of charge of the energy store, neither a charge balancing has to be undertaken, nor has an impedance model to be stored.

Ascertaining an operating state such as, for instance, the state of charge, of the energy store system or the cell element may further take place, in this instance, particularly during the operation of the energy store system. Within the meaning of the present invention, this may particularly mean that the energy store is in a charging or state of discharge. However, it is also possible that the energy store is not necessarily in a charging or state of discharge, as long as it is located at its place of application. In other words, ascertaining an operating state during the operation may mean that the energy store does not have to be in maintenance or the like, but is, in particular, directly available for a charging or discharging process.

In order to ascertain a state of charge of the cell element or of the energy store, the energy store system according to the present invention may particularly have an analytical unit, by which at least one property of the functional material and/or electrolyte system is able to be analyzed for the qualitative and/or quantitative ascertainment of the functional material situated or formed and decomposed in the electrolyte system. The state of charge is able to be ascertained at any desired time, in particular, by a direct analysis of at least one property of the functional material and/or of the electrolyte system by an analytical unit, in a particularly accurate and dynamic manner. The electrical conductivity or the viscosity, for example are suitable as the analyzable property of the electrolyte system.

Within the scope of an additional embodiment, the energy store system may have a light source by which the electrolyte system is able to be irradiated at least partially, and the energy store system may have a detector by which the absorption of the irradiated electrolyte system is able to be analyzed. Consequently, in this embodiment, an analytical unit may particularly be formed by the light source and the detector. In this embodiment, the electrolyte system and, with that, particularly functional material situated in it may be investigated especially by the absorption behavior or the absorbance behavior of the electrolyte system or rather the functional material. In detail, the electrolyte system may be irradiated using light of a suitable wavelength, and the absorption behavior, which is a function of the type and the quantity of dissolved functional material, may be investigated by a suitable detector. One investigation or analysis of the absorption behavior includes, in a manner understandable by one skilled in the art, in this case, an investigation or analysis of the absorbance behavior of the electrolyte system.

For the not limiting example of a lithium sulfur battery, the elementary sulfur is reduced via a plurality of polysulfide intermediate stages to the end products lithium disulfide ($Li_2S_2$) and lithium sulfide ($Li_2S$) in the following manner:

$$Li+S \rightarrow Li_2S_x (3 \leq x \leq 8) \rightarrow Li_2S_2 + Li_2S.$$

In this instance, the first intermediate stage $Li_2S_x$ is well soluble in a conventional electrolyte system, whereas the end products, lithium disulfide ($Li_2S_2$) and lithium sulfide ($Li_2S$), are soluble with difficulty or not at all in a conventional electrolyte system, and consequently precipitate out.

As a conventional exemplary electrolyte system, one may use, in this case, for instance, 3-dioxolane (DOL)/dimethoxyethane (DME) with lithium-bis-(trifluoromethylsulfonyl-imide) (LiTFSI) as electrolyte. In this electrolyte system, lithium disulfide and lithium sulfide are poorly soluble and precipitate especially in the cathode structure. This may typically include elementary sulfur, a conductive additive, such as soot and graphite, as well as a binder, such as polyvinylidene fluoride (PVDF), teflon or a cellulose-based system. The polysulfides $Li_2S_x$, in which x may be in a range of $3 \leq x \leq 8$, are soluble in the electrolyte system. In this context, the color of the solution, or rather the electrolyte system changes as a function of the sulfur chain length of the polysulfides. Accordingly, each polysulfide demonstrates characteristic bands, such as, particularly, absorption bands, which are able to be analyzed and evaluated by an analysis of the absorbance behavior.

Such properties may be utilized in order to determine the state of charge of the cell via a measurement of the absorbance or the absorption, by a corresponding selection of excitation wavelengths, such as, for instance, a selection of the absorption maxima of various polysulfide reference solutions of different charging and discharging states. As was stated above, in this instance, within the scope of the present invention, besides the pure absorption, an evaluation of the entire absorbance is possible, which also demonstrates a clear dependence on the discharging depth. In detail, within the meaning of the present invention, one would understand by total absorbance the integral of the absorbance over a definite wavelength range.

Particularly by an optical analysis of the electrolyte system or the functional material, the problem of a faulty current integration as well as a difficult impedance modeling of the cell may be circumvented.

In this context, one skilled in the art will understand that the above examples are used purely for illustration and description of this exemplary embodiment. The present invention and this exemplary embodiment is thus in no way limited to the abovementioned examples, such as, in particular, a lithium sulfur cell.

Within the scope of a further embodiment, a detection range situated outside the cell region and including an electrolyte system may be provided for the qualitative and/or quantitative ascertainment of functional material situated in the electrolyte system. In this embodiment, the electrolyte system is thus not located exclusively in the cell region, but additionally in a further region that is particularly provided only for a detection and analysis of the electrolyte system or the functional material. Consequently, within the meaning of the present invention, a detection region may particularly be a region or a space which is not, or not directly situated between an anode and a cathode. Since, however, in this region an electrolyte system is situated in which, for example, based on diffusion effects, functional material is also present, such a region is particularly suitable in a cost-effective manner for the analysis of the electrolyte system. In this context, the detection region may, for instance, be able to be irradiated at least partially by a light source, and the absorbance behavior may be able to be ascertained by the detector. By contrast, the anode and the cathode may be formed in the conventional manner, without this having to permit an optical path, for example, of a light source through the cell region.

Within the scope of another embodiment, the anode and the cathode may each have a light-transmitting region aligned to each other that is able to be transilluminated by the light source. Thus, in this embodiment the functional material may be analyzed which is located directly in the cell region. This advantageously enables a particularly accurate analysis of the functional material. In addition, because a measurement is able to be implemented directly at the potential location of the creation of detectable functional material, a particularly dynamic and rapid analysis is possible. In the case in which a separator is situated between the anode and the cathode, it expediently also has a light-transmitting region which is aligned towards the light-transmitting region of the anode and the cathode, in order to permit a continuous optical path of the light source.

Within the scope of another embodiment, the cell region, the analytical unit and particularly the detection region may be surrounded by a housing. In this embodiment, essentially the entire energy store system may thus be surrounded by a housing, and may thus be combined to form a protected component. In this embodiment, the entire energy store system may thus be protected from outer influences, and may thus operate particularly securely and reliably. In addition, an exchange of the energy store system, according to the present invention, such as in the case of a defect in this embodiment, may be made particularly simply.

Within the scope of yet another embodiment, the cell region may be surrounded by a housing, the housing being able to have at least one light-transmitting region, for the outer positioning of the analytical unit. In this embodiment, an energy store may be used that is thus essentially a commercial energy store, which is changed only in that it is light-transmitting at a suitable place in the housing, or rather has a light-transmitting region. Thereby, at this region, in particular, a light source and/or a detector are able to be situated as an analytical unit, so that an analysis of the electrolyte system is made possible. In this context, it is understandable to one skilled in the art that, depending on the situation of the light source and/or the detector and the optical path of the light source, a plurality, particularly two light-transmitting regions may be provided. The housing may be light-transmitting at the detection region, for example. Thereby, also in this embodiment, the detection region may be used for an analysis of the electrolyte system. Moreover, the light-transmitting region(s) may be aligned with respect to the optical path through the cell region. It is further understandable that in the abovementioned embodiment, correspondingly aligned light-transmitting regions may also be provided in the electrodes and the separator, if necessary.

In this embodiment, the analytical unit may be decoupled from the cell region, for instance, or the detection region as such, so that the use of an analytical unit for a plurality of cells or cell elements may also be made, which is especially cost-effective. In addition, a particularly simple contacting of the analytical unit may be implemented.

Within the scope of still one more embodiment, the light source may include a light-emitting diode and/or the detector may include a phototransistor. A light-emitting diode is produced cost-effectively and has a long service life, which ensures a particularly reliable functioning of the energy store system. In addition, light-emitting diodes are able to be developed to be very compact, whereby these are also able to be integrated into tight spatial conditions, such as particularly into a compact energy store system, without a problem. Furthermore, because of light-emitting diodes, particularly as a function of the semiconductor material, light may be generated having a wavelength by which suitable absorption bands are detectable in many different energy stores, such as in lithium sulfur batteries. In addition, phototransistors are also able to be developed in an especially compact manner, and thereby make possible a very accurate analysis of especially the absorbance behavior or the absorption behavior of the electrolyte system and the functional material.

Within the scope of a further embodiment, light may be able to be emitted by the light source in a wavelength range of the spectrum of the UV/VIS range. In this embodiment, the present invention may be useful for a plurality of cells or energy stores used. As a non-limiting example, particularly polysulfides of different chain lengths, which occur in a charging or discharging process of a lithium sulfur battery, have characteristic bands in the spectrum of the UV/VIS range. The UV/VIS range may, in this case, within the meaning of the present invention, include particularly light having a wavelength of ≥1 nm to ≤800 nm.

The subject matter of the present invention is also a state detection system, including an energy store system according to the present invention, further having an evaluation unit and/or processing unit. Such a state detection system is able to ascertain in a particularly simpla manner an operating state, such as particularly the state of charge or the aging state of an energy store or a cell element. For this purpose, the state detection system may include an evaluation unit, for example, in which, for instance, corresponding operating models such as charging models or aging models are stored, If the values ascertained, for instance, by a analytical unit, such as the detector, are compared to the stored model, one may conclude in a simple manner upon the operating state of the energy store. An automated detection of an operating state may further take place because of the processing unit.

Going into details, with regard to the advantages of the state detection system according to the present invention, we point to the statements with respect to the energy store system according to the present invention.

Further advantages and advantageous refinements of the subject matters of the present invention are illustrated by the drawings and elucidated in the following description. It should be noted that the drawings have only a descriptive character and are not intended to limit the invention in any form.

DETAILED DESCRIPTION

Figure 1:
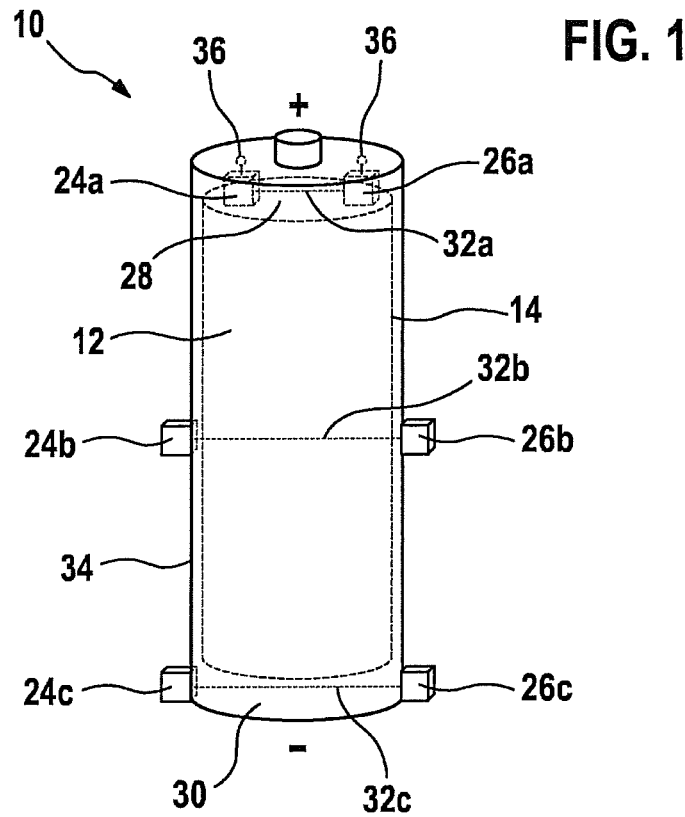
FIG. 1 shows a schematic representation of various specific embodiments of an energy store system according to the present invention.

FIG. 1 shows a schematic view, which is intended to represent various specific embodiments of energy store system 10 according to the present invention. Energy store system 10 according to the present invention may be used, for instance, in any type of mobile or stationary applications, in which particularly a high specific energy may be essential. As non-limiting examples, energy store system 10 according to the present invention may be used in tools, computers, hybrid vehicles and plug-in hybrid vehicles or even in purely electrically driven vehicles. Energy store system 10 according to the present invention may be used in connection with energy stores which are distinguished by a particularly high specific energy, such as lithium-based energy stores such as lithium sulfur batteries.

Energy store system 10 according to the present invention may further be a part of a state detection system. In this context, the state detection system, such as particularly a battery management system, may further have an evaluation unit and/or a processing unit. Thereby, in a suitable manner, perhaps in the evaluation unit, for instance, various states of charge or properties connected to these, of the electrolyte system, such as particularly calibrated comparison values may be stored, so that an exact evaluation of the state of charge, for example, may take place. In addition, a particularly completely automated ascertainment may take place of the state of charge, for example, by the processing unit.

Energy store system 10 according to the present invention includes at least one cell element 14 situated in its cell region 12. Cell element 14 has an anode 16, a cathode 18 and an electrolyte system 20, that is particularly at least partially liquid, situated between anode 16 and cathode 18. In an energy store 10 developed in a cylindrical form, for example, cell element 14 may be configured as a cell reel.

Figure 2:
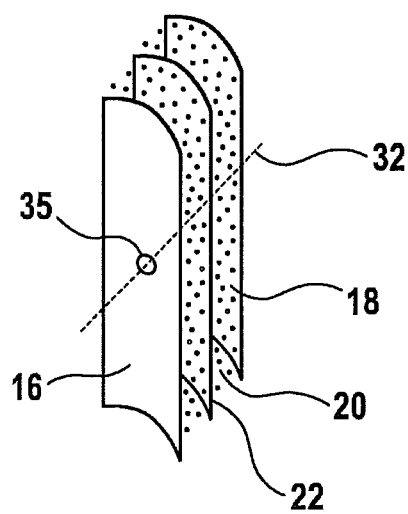
FIG. 2 shows a detailed view of the energy store system from FIG. 1.

A partial view of the cell reel is shown in FIG. 2. In FIG. 2 it may also be recognized that between anode 16 and cathode 18 a separator 22 may be provided, which is particularly able to effect an electrical separation of anode 16 and cathode 18.

According to the present invention, anode 16 and cathode 18 and/or electrolyte system 20 are developed so that, as a function of a charging and/or discharging process of cell element 14, functional material is situated in electrolyte system 20. Furthermore, the functional material situated in electrolyte system 20 is ascertainable qualitatively and/or quantitatively.

For this, energy store system 10 may, for instance, further have an analytical unit, by which particularly at least one property of the functional material is able to be analyzed for the qualitative and/or quantitative ascertainment of the particularly dissolved or dispersed functional material situated in electrolyte system 20. In one specific embodiment, energy store system 10 may for instance have a device for carrying out an ATR-IR spectroscopic analysis. A light guide may be provided, for example, through which light is guided which interacts with functional material that is situated outside the light guide, such as dispersed functional material. Alternatively or in addition, energy store system 10 is able to have one or a plurality of light sources 24, by which electrolyte system 20 is able to be at least partially irradiated. Furthermore, energy store system 10 may have one or a plurality of detectors 26 by which one is able to analyze the absorption and the absorbance of the functional material situated in electrolyte system 20. Light source 24 may then include or be a light-emitting diode, whereas detector 26 may include a phototransistor, or rather be one. Moreover, it may be advantageous if, because of light source 24, light is able to be emitted in a wavelength range of the spectrum of the UV/VIS range. In FIG. 1, three exemplary possibilities are shown for this, for positioning the analytical unit, particularly light source 24 and detector 26. In this context, the specific embodiments shown in FIG. 1 are able to be used alternatively or together and are not limiting.

According to FIG. 1, a detection range 28, 30 situated outside cell region 12 and including electrolyte system 20 may be provided for the qualitative and/or quantitative ascertainment of functional material situated in electrolyte system 20. Detection range 28, 30 may have a height in a range of ≥1 mm, in this context.

This may mean especially that cell region 12 and cell element 14 do not close flush with housing 34. Detection region 28 may be situated, for instance, above cell element 14 or cell region 12, that is, for example, at the plus pole, whereas detection region 30 may be situated below cell element 14 and cell region 12, for example, that is, for instance, at the minus pole. In this case, the analytical unit may have a light source 24a and a detector 26a in detection region 28, for example, light source 24a emitting a light beam 32a to detector 26a. In such an embodiment of light source 24 and detector 26, thus, cell region 12, the analytical unit and particularly detection region 28 may be surrounded by an, in particular, hard housing 34. This embodiment assumes a suitable contacting 36 of light source 24 and detector 26 within housing 34.

Furthermore, the analytical unit may have a light source 24c and a detector 26c, for example, light source 24c emitting a light beam 32c to detector 26c. In this context, light source 24c and detector 26c may be situated outside housing 34, light beam 32c, however, running through detection region 30.

In a further specific embodiment, a light source 24b and a detector 26b may be situated at the height of cell region 12. In this embodiment, light beam 32b thus runs through cell region 12 and, with that, through cell element 14, such as through the cell reel. In this context, light source 24b and detector 26b may be situated within or outside of housing 34.

In addition, it may be of advantage if anode 16 and cathode 18 and perhaps separator 22 and housing 34 have a light-transmitting, for instance, perforated region 35, situated respectively aligned to one another, which is penetrable by radiation from light source 24, or through which light beam 32 is able to run. In this context, light-transmitting region 35 may be developed, for instance, as a perforation or as a corresponding opening or hole, which has a diameter in a range of ≥0.5 mm to ≤5 mm, particularly ≥1 mm to ≤3 mm. This is illustrated in FIG. 2. In this context, it may be of advantage if light-transmitting region 35 of separator 22 has a smaller size or a smaller diameter than that of anode 16 and cathode 18, in order thus to prevent the touching of the electrodes and thus a short circuit. For instance, light-transmitting region 35 of separator 22 may be smaller by ≥0.1 mm to ≤1 mm, or rather have a smaller diameter than the diameter of light-transmitting region 35 of anode 16 and cathode 18.

In particular, in the case of the situation of light source 24 and detector 26 outside housing 34, cell region 12 is thus surrounded by housing 34, housing 34 having at least one light-transmitting region 35 for situating the analytical unit, such as light source 24 and detector 26.

Figure 3:
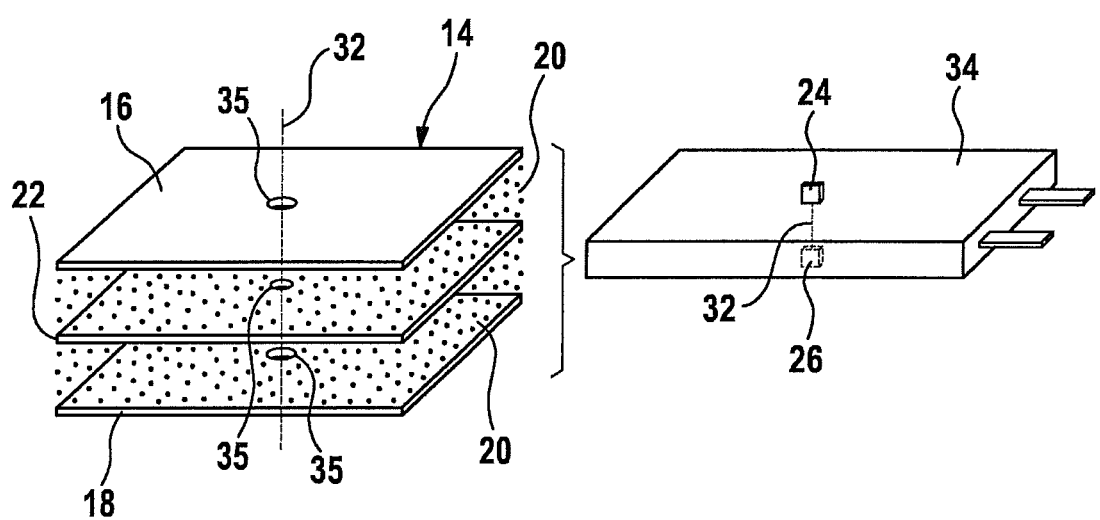
FIG. 3 schematically shows a cell element of another specific embodiment of the energy store system according to the present invention.

FIG. 3 shows a further partial view of an energy store 10 according to the present invention. According to FIG. 3, cell element 14 includes particularly an anode 16, cathode 18 and separator 22 situated in parallel to one another and configured plate-like, between anode 16 and cathode 18, in turn, electrolyte material 20 being situated. In this context, in the same way as with respect to FIG. 1 and FIG. 2, a plurality of units including anode 16, cathode 18 and electrolyte system 20, and particularly separator 22, may be arranged one over the other. In the case of a cell reel according to FIG. 1, the units may be wound, for instance, one over the other, whereas, according to FIG. 3, they are able to be laid or folded one over the other. According to FIG. 3, anode 16, cathode 18 and separator 22, in turn, have a light-transmitting region 35, through which there runs a light beam 32 of a light source 24. In this context, even if housing 34 has one or two light-transmitting regions 35, light source 24 and detector 26 may be situated outside housing 34. Moreover, housing 34 may, in the case of a prismatic cell element 14, be embodied to be hard, for example, for instance, made of stainless steel, whereas, in the case of a so-called pouch form, it may be configured to be elastic. In the latter form, for instance, it may be constructed of aluminum foil coated with a non-conductive plastic, such as polyethylene or polypropylene. In this context, anode 16, cathode 18 and perhaps separator 22 corresponding to a prismatic cell or a pouch form.

An energy store system 10, according to the present invention, particularly permits, by an analysis of the functional material, enabling especially a qualitative and/or quantitative investigation of the functional material situated in electrolyte system 20. Thereby a determination of an operating state may be made possible, such as especially a state of charge of the cell or cell element 14. An optical analysis of electrolyte system 20 or of the functional material situated in electrolyte system 20 may particularly be of advantage, for instance, by the investigation of the UV/VIS spectrum of the functional material.

Figure 4:
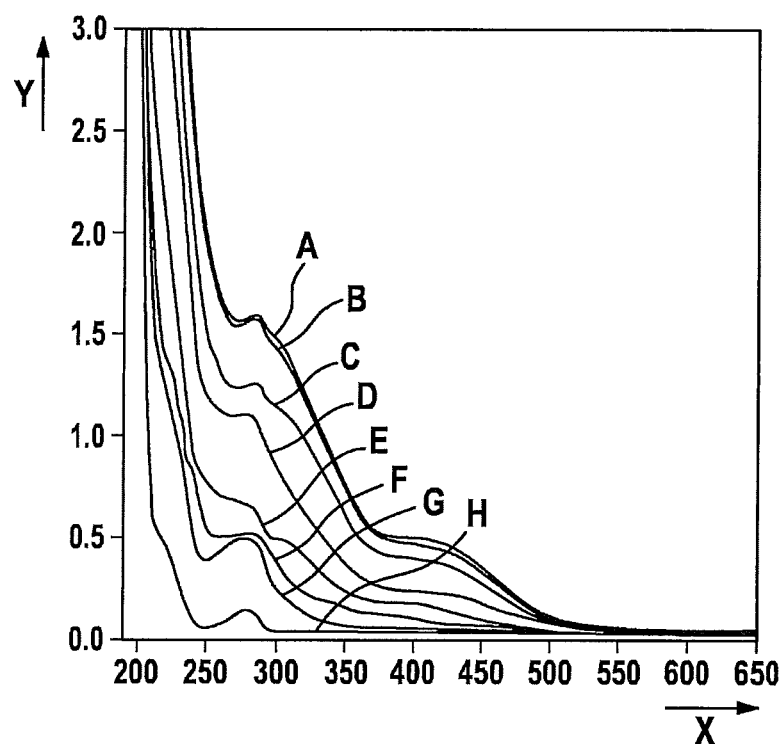
FIG. 4 is a diagram showing different characteristic absorption bands in a UV/VIS spectrum.
Figure 5:
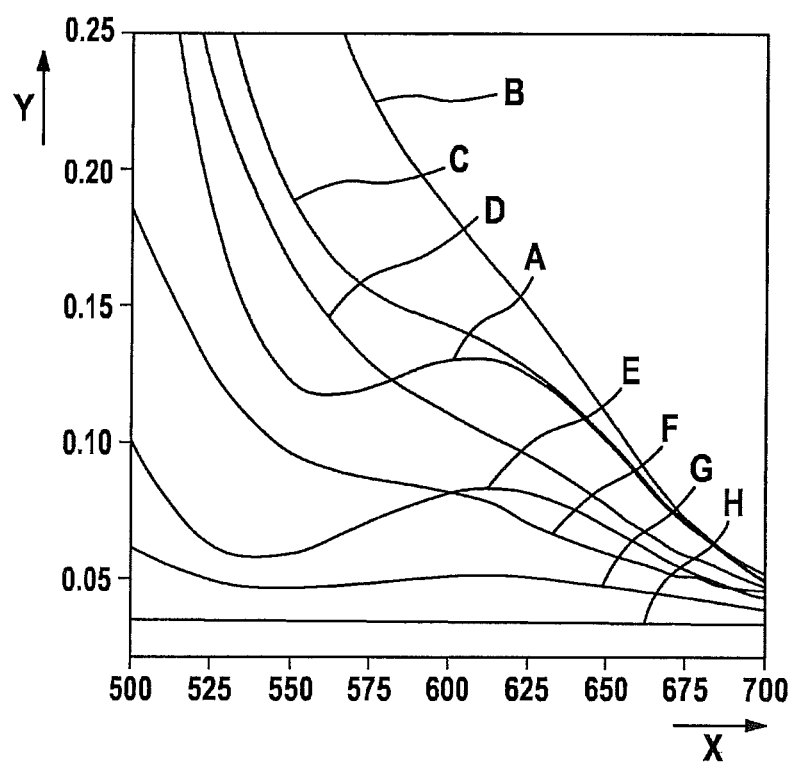
FIG. 5 is an enlarged view of the diagram from FIG. 4.

FIG. 4 shows different characteristic absorption bands, which were ascertained for different polysulfides, or rather for polysulfides present at different states of charge. An enlarged partial view in a wavelength range of 500 nm to 700 nm is shown in FIG. 5, in this context. The wavelength in nanometers is plotted on the X axis, whereas the Y axis shows the absorption, in each case without dimension.

In this context, line A corresponds to a discharge state of 22%, line B corresponds to a discharge state of 14%, line C corresponds to a discharge state of 40%, line D corresponds to a discharge state of 8%, line E corresponds to a discharge state of 57%, line F corresponds to a discharge state of 0%, line G corresponds to a discharge state of 61% and line H corresponds to the solvent dimethyl ether (DME) with a clean electrolyte system without functional material, overall a dilution of an electrolyte solution (DME/DOL: 1/1 having been used, while adding 1M LiTFSI) in the solvent in a ratio of 1:4. In this case, the discharge state further describes the state of a discharge in relation to the theoretically possible capacitance. In the case of a lithium sulfur cell this means, for instance, that the sulfur was totally utilized. The state of charge in relation the theoretically possible capacitance of sulfur may therefore be ascertained as follows: State of charge=100%−state of discharge. The actual state of charge is yielded by 100%*(1−(state of discharge/sulfur utilization)). In this context, the abovementioned measurements were based, in particular, on an extraction of a separator 22 with 2 ml of dimethyl ether, this extract being diluted again with pure dimethyl ether in a ratio of 1:4.

Figure 6:
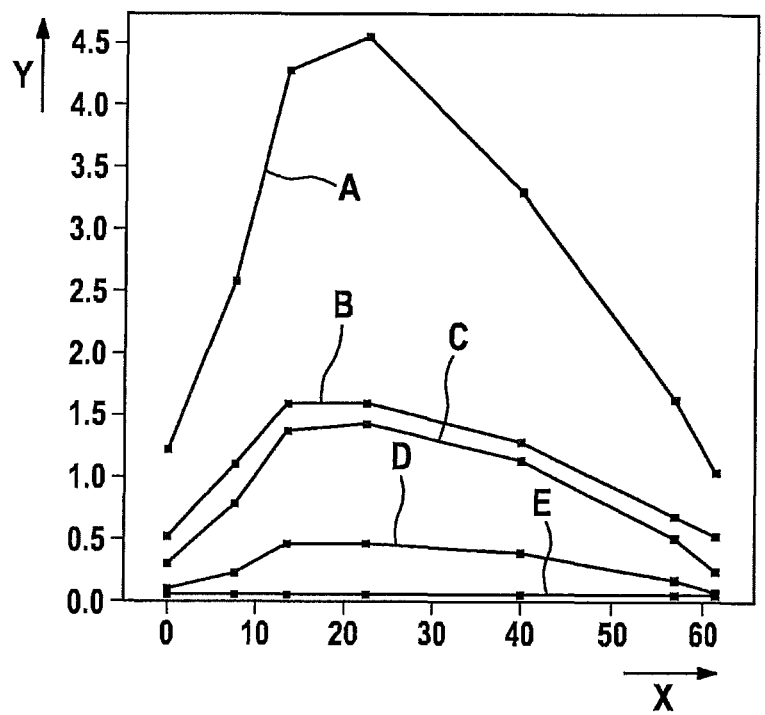
FIG. 6 shows an exemplary absorption behavior of an electrolyte system at different wavelengths as a function of the state of charge.

FIG. 6 also shows an exemplary absorption behavior of a functional material situated in an electrolyte system 20 at different excitation wavelengths as a function of the state of charge. In this context, the state of discharge in % is plotted on the X axis, with reference to the theoretical overall capacitance, whereas the Y axis shows the absorption intensity. Here, line A corresponds to a wavelength of 228 nm, line B to a wavelength of 280 nm, line C to a wavelength of 305 nm, line D to a wavelength of 420 nm and line E to a wavelength of 620 nm. In this figure one may recognize that, with reference to this electrolyte system and this cell element 14, a wide range of excitation wavelengths is possible, but that an excitation wavelength of 228 nm may be used.

Figure 7:
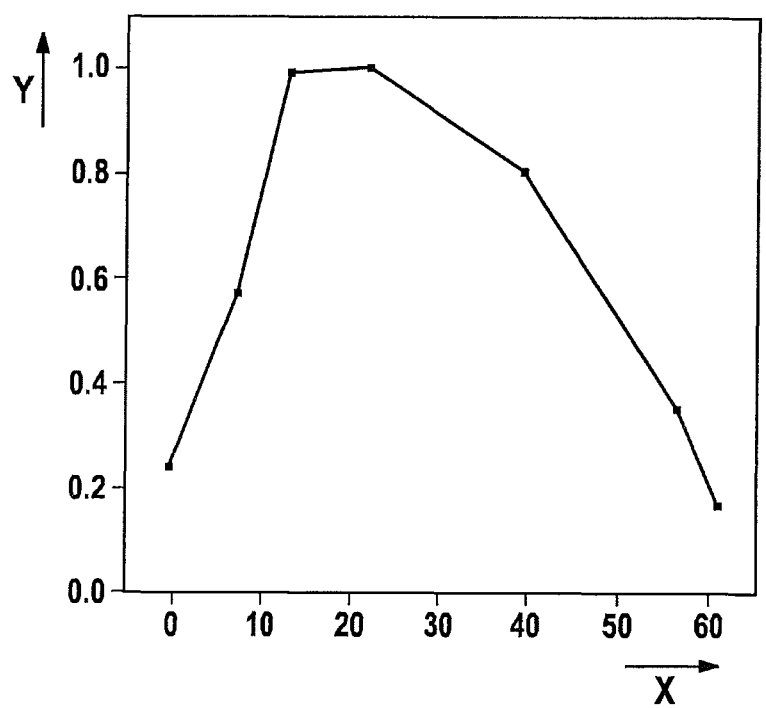
FIG. 7 shows an exemplary total absorption as a function of the state of charge.

FIG. 7 further shows the overall absorbance, that is, the absorbance over a wavelength of 280 nm to 900 nm on the Y axis plotted against the state of discharge in %, with reference to the theoretical overall capacitance of cell element 14 on the X axis.

If, besides the state of charge, the current internal resistance and the capacitance are known, an estimation of state data, such as stored and storable energy, the maximum charging power and discharging power, the aging state (state of health, SOH) and even the functional state (state of function, SOF) may be ascertained from this state information, based on knowledge of the properties of the energy store.

What is claimed is:

1. An energy store system, comprising:
   at least one cell element situated in a cell region, having an anode, a cathode and an electrolyte system, situated between the anode and the cathode, that is at least partially liquid, wherein the anode and the cathode each have a light transmitting region, the light transmitting region of the anode being aligned with the light transmitting region of the cathode;
   wherein at least one of the anode, the cathode and the electrolyte system are configured so that, as a function of at least one of a charging process and a discharging process of the cell element, functional material is situated in the electrolyte system, and the functional material situated in the electrolyte system is ascertainable at least one of qualitatively and quantitatively;
   a light source by which the electrolyte system is at least partially irradiated through the aligned light transmitting regions of the anode and the cathode; and
   a detector by which the absorption of the irradiated electrolyte system is analyzable via light from the light source, wherein the anode and the cathode are situated between the light source and the detector.

2. The energy store system of claim 1, further comprising:
   an analytical unit, including the light source and the detector, by which at least one property of at least one of the functional material and the electrolyte system is analyzable for at least one of the qualitative and quantitative ascertainment of the functional material situated in electrolyte system.

3. The energy store system of claim 1, wherein there is a detection range, situated outside a cell region and including the electrolyte system, for the at least one of the qualitative and quantitative ascertainment of functional material situated in the electrolyte system.

4. The energy store system of claim 2, wherein the cell region, and the analytical unit are surrounded by a housing.

5. The energy store system of claim 1, wherein the cell region is surrounded by a housing, which has at least one light-transmitting region aligned with the aligned light transmitting regions of the anode and the cathode, the light source and the detector being positioned on an outside of the housing.

6. The energy store system of claim 1, wherein at least one of the following is satisfied: (ii) the light source includes a light-emitting diode; and (ii) the detector includes a phototransistor.

7. The energy store system of claim 1, wherein the light source emits light in a wavelength range of the spectrum of the UV/VIS range.

8. The energy store system as recited in claim 1, wherein the cell element is a cylindrical cell reel.

9. The energy store system as recited in claim 1, wherein the anode and the cathode are plates situated parallel to one another.

10. The energy store system as recited in claim 1, wherein the anode, the cathode, and the electrolyte system are situated together in a single housing.

11. The energy store system as recited in claim 1, wherein the light source and the detector are aligned with the aligned light transmitting regions of the anode and the cathode.

12. A state detection system, comprising:
    an energy store system, including:
    at least one cell element situated in a cell region, having an anode, a cathode and an electrolyte system, situated between the anode and the cathode, that is at least partially liquid, wherein the anode and the cathode each have a light transmitting region, the light transmitting region of the anode being aligned with the light transmitting region of the cathode;
    wherein at least one of the anode, the cathode and the electrolyte system are configured so that, as a function of at least one of a charging process and a discharging process of the cell element, functional material is situated in the electrolyte system, and the functional material situated in the electrolyte system is ascertainable at least one of qualitatively and quantitatively;
    a light source by which the electrolyte system is at least partially irradiated through the aligned light transmitting regions of the anode and the cathode; and
    a detector by which the absorption of the irradiated electrolyte system is analyzable via light from the light source, wherein the anode and the cathode are situated between the light source and the detector; and
    an evaluation unit.

13. The state detection system as recited in claim 12, wherein the cell element is a cylindrical cell reel.

14. The state detection system as recited in claim 12, wherein the anode and the cathode are plates situated parallel to one another.

15. The state detection system as recited in claim 12, wherein the anode, the cathode, and the electrolyte system are situated together in a single housing.

16. The state detection system as recited in claim 12, wherein the light source and the detector are aligned with the aligned light transmitting regions of the anode and the cathode.

* * * * *